United States Patent
Voskoboynikov et al.

(10) Patent No.: US 6,756,340 B2
(45) Date of Patent: Jun. 29, 2004

(54) DEHYDROGENATION CATALYST COMPOSITION

(75) Inventors: Timur V. Voskoboynikov, Arlington Heights, IL (US); Daniel H. Wei, Naperville, IL (US); J. W. Adriaan Sachtler, Des Plaines, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/118,642

(22) Filed: Apr. 8, 2002

(65) Prior Publication Data

US 2003/0191351 A1 Oct. 9, 2003

(51) Int. Cl.[7] ............................................. B01J 23/58
(52) U.S. Cl. ....................................... 502/328; 502/330
(58) Field of Search ............................... 502/327, 328, 502/330, 332, 334, 339, 355, 415, 439

(56) References Cited

U.S. PATENT DOCUMENTS

| | | | | |
|---|---|---|---|---|
| 4,070,413 A | | 1/1978 | Imai ........................ 260/683.3 |
| 4,119,567 A | * | 10/1978 | Bartsch ........................ 252/430 |
| 4,136,064 A | * | 1/1979 | Hayes et al. ............. 252/466 B |
| 4,199,437 A | * | 4/1980 | Courty et al. ............... 208/124 |
| 4,207,169 A | * | 6/1980 | Courty et al. ............... 208/124 |
| 4,358,399 A | * | 11/1982 | Antos ........................... 252/441 |
| 4,366,091 A | * | 12/1982 | Antos .................... 252/466 PT |
| 4,608,360 A | | 8/1986 | Abrevaya et al. ........... 502/226 |
| 4,717,779 A | | 1/1988 | Bricker et al. .............. 585/443 |
| 4,786,625 A | | 11/1988 | Imai et al. ................... 502/326 |
| 4,788,371 A | | 11/1988 | Imai et al. ................... 585/443 |
| 4,914,075 A | | 4/1990 | Bricker et al. .............. 503/330 |
| 5,439,865 A | * | 8/1995 | Abe et al. .................... 502/333 |
| 5,482,910 A | * | 1/1996 | Bricker et al. .............. 502/300 |
| 5,665,223 A | * | 9/1997 | Bogdan ....................... 208/138 |
| 5,858,908 A | * | 1/1999 | Bogdan et al. ............. 502/227 |
| 5,883,039 A | * | 3/1999 | McBride, Jr. et al. ...... 502/327 |
| 6,087,295 A | * | 7/2000 | Kharas et al. .............. 502/300 |
| 6,177,381 B1 | * | 1/2001 | Jensen et al. ............... 502/325 |
| 6,414,209 B1 | * | 7/2002 | Herskowitz et al. ........ 585/661 |
| 6,495,487 B1 | * | 12/2002 | Bogdan ....................... 502/227 |

FOREIGN PATENT DOCUMENTS

EP 0 782 884 A1 7/1997 ............ B01J/37/02

* cited by examiner

*Primary Examiner*—Steven Bos
*Assistant Examiner*—Cam Nguyen
(74) *Attorney, Agent, or Firm*—John G. Tolomei; James C. Paschall; John G. Cutts

(57) ABSTRACT

A novel catalyst composite is disclosed. Also disclosed is a use for the novel composite. The catalyst composite comprises a Group VIII noble metal component, a Group IA or IIA metal component, and a component selected from the group consisting of tin, germanium, lead, indium, gallium, thallium, or mixtures thereof, all on an alumina support comprising essentially theta-alumina, having a surface area from about 50 to about 120 $m^2/g$, an apparent bulk density of at 0.5 $g/cm^3$ and a mole ratio of the Group VIII noble metal component to the component selected from the group consisting of tin, germanium, lead, indium, gallium, thallium or mixtures thereof in the range from about 1.5 to about 1.7.

7 Claims, 1 Drawing Sheet

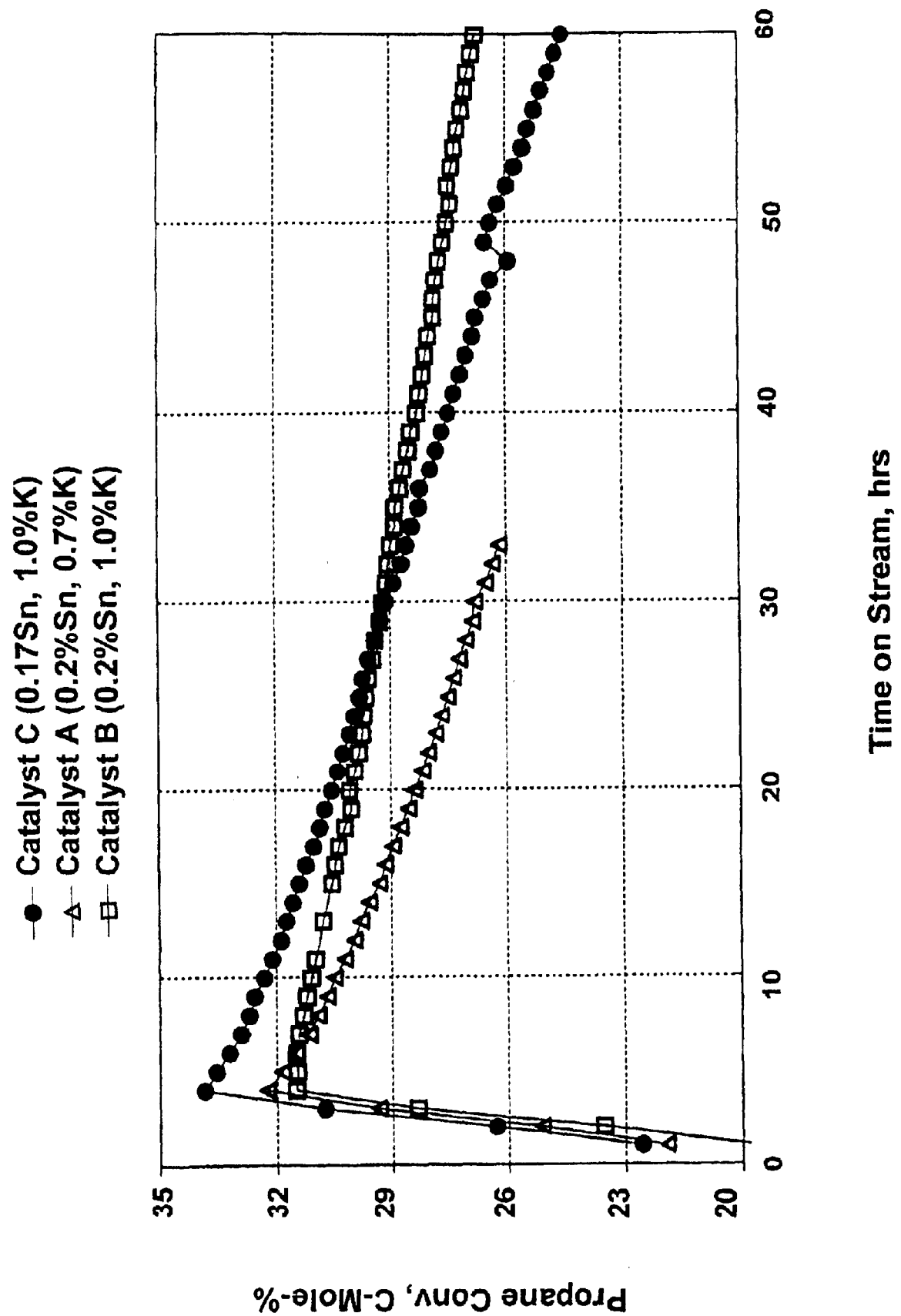

DEHYDROGENATION CATALYST COMPOSITION

BACKGROUND OF THE INVENTION

This invention relates to the conversion of hydrocarbons, especially the dehydrogenation of dehydrogenatable hydrocarbons, in the presence of a catalyst composite. This invention also pertains to a new catalyst composite.

The dehydrogenation of hydrocarbons is an important commercial process because of the great demand for dehydrogenated hydrocarbons for the manufacture of various chemical products such as detergents, high octane gasolines, pharmaceutical products, plastics, synthetic rubbers, and other products well known to those skilled in the art. One example of this process is dehydrogenating isobutane to produce isobutylene which can be polymerized to provide tackifying agents for adhesives, viscosity-index additives for motor oils, impact-resistant and anti-oxidant additives for plastics and a component for oligomerized gasoline.

INFORMATION DISCLOSURE

The prior art is cognizant of various catalytic composites which contain a Group VIII noble metal component, an alkali or alkaline earth metal component, and a component selected from the group consisting of tin, germanium, lead, indium, gallium, thallium, or mixtures thereof. However, the prior art has not yet known of a catalyst composite having a surface area of 120 $m^2/g$ or less, having an ABD of 0.5 $g/cm^3$ or greater and a mole ratio of the Group VIII noble metal component to the component selected from the group consisting of tin, germanium, lead, indium, gallium, thallium or mixtures thereof in the range from about 1.5 to about 1.7.

U.S. Pat. No. 4,070,413 describes a dehydrogenation process utilizing a catalyst comprising a Group VIII metal and lithium, both impregnated on an alumina support. The alumina support is further characterized in that it has been hydrothermally treated in steam at a temperature from about 800° to 1200° C. The catalyst of this invention is distinguished from that of the '413 patent in that the instant catalyst comprises, in addition to a Group VIII metal component and an alkali or alkaline earth metal component, a component selected from the group consisting of tin, germanium, lead, indium, gallium, thallium, or mixtures thereof. Additionally, the catalyst support of this invention has a higher ABD than that disclosed in the '413 patent. The '413 patent discloses a catalyst having a pre-hydrothermally treated ABD of from about 0.25 to about 0.45 $g/cm^3$. From Example III, it is seen that the final catalyst composites of the catalyst of the U.S. Pat. No. '413 have an ABD of about 0.3. The catalyst of this invention must have a final ABD of at least 0.5 $g/cm^3$.

U.S. Pat. No. 4,608,360 describes a catalytic composite comprising a Group VIII noble metal component, a co-formed IVA metal component, and an alkali or alkaline earth metal on an alumina support having a surface area of from 5 to 150 $m^2/g$. Additionally, the alumina support of the '360 patent is characterized in that the mean pore diameter is about 300 angstroms or less and more than about 55% of the total pore volume of the support is associated with pores having a mean diameter of 600 angstroms or more. In distinction, the catalyst of this invention is characterized in that it has a surface area of 120 $m^2/g$ or less and an ABD of 0.5 $g/cm^3$ or more. The catalyst of the '360 patent from Example II has an ABD of about 0.3. Additionally, the catalyst of the present invention contains very little of its total pore volume in pores having a diameter of 600 angstroms or more while the '360 catalyst has over 50% of its total pore volume associated with pores having mean diameters of about 600 angstroms or more.

U.S. Pat. No. 4,717,779 discloses a process for dehydrogenating dehydrogenatable hydrocarbons using a selective oxidation catalyst comprising a Group VIII noble metal component, a Group IVA component, and if desired a Group IA or IIA component. The components are composited on an alumina support wherein an alumina precursor possesses an ABD less than about 0.6 $g/cm^3$ which, after calcination at a temperature of from about 900° to 1500° C., will result in an alumina possessing an ABD of from 0.3 to 1.1 $g/cm^3$ and where more than 40% of the pore volume is present in pores greater than 1500 angstroms. In contrast, the catalyst of the present invention comprises an ABD of 0.5 $g/cm^3$ or greater and preferably from 0.6 $g/cm^3$ or greater and a mole ratio of the Group VIII noble metal component to the Group IVA, Group IA or IIA component is in the range from about 1.5 to about 1.7. Additionally, very little of the total catalyst pore volume, that is, much less than 40% of the total catalyst pore volume, is comprised of pores of 1500 angstroms or greater.

U.S. Pat. No. 4,786,625, discloses a catalyst for the dehydrogenation of dehydrogenatable hydrocarbons comprising a platinum group metal component, a modifier metal component selected from the group consisting of tin, germanium, rhenium, and mixtures thereof, and optionally an alkali or alkaline earth metal component, all on a refractory oxide support, preferably alumina. The catalyst is characterized in that the platinum group metal component is surface impregnated. The catalyst of the present invention does not comprise any surface-impregnated components and, in addition, the alumina catalyst support of the '625 patent is not characterized as requiring a limited ABD or surface area.

U.S. Pat. No. 4,788,371, discloses a catalytic oxidative steam dehydrogenation process utilizing a single catalyst comprising a Group VIII noble metal component; one or more components selected from the group consisting of lithium, sodium, potassium, rubidium, cesium, and francium; and one or more components selected from the group consisting of boron, gallium, indium, thallium, germanium, tin, and lead, all on an inorganic oxide support, preferably alumina having a surface area of from 1 to 500 $m^2/g$, but preferably from 5 to 120 $m^2/g$. The catalyst does not disclose a specific range for the alumina support.

U.S. Pat. No. 4,914,075 discloses a catalytic composite comprising a Group VIII noble metal component, a Group IA or IIA metal component and a component selected from the group consisting of tin, germanium lead, indium, gallium, thallium or mixtures thereof, all on an alumina support having a low surface area of 120 $m^2/g$ or less and an ABD of 0.5 $g/cm^3$ or more. This reference discloses a catalyst which has a platinum to tin mole ratio of 0.914.

The present invention is a catalytic composite and process for its use with the catalyst having a support with a surface area of 120 $m^2/g$ or less in conjunction with an apparent bulk density (ABD) of at least 0.5 $g/cm^3$. The support is utilized in conjunction with a platinum group metal component, an alkali or alkaline metal component and a third component selected from the group consisting of tin, germanium, lead, indium, gallium, thallium and mixtures thereof. It has surprisingly been discovered that a superior catalyst, which possesses an alkali or alkaline metal component in an amount from 0.9 to 1.1 weight percent based on the total composite weight and a mole ratio of the platinum group metal component to the third component from about 1.5 to about 1.7, demonstrates a higher initial maximum hydrocarbon dehydrogenation activity and a higher conversion from 5 to 20 hours on stream.

OBJECTS AND EMBODIMENTS

It is an object of the present invention to provide an improved catalytic composite and a process for the conversion of hydrocarbons and especially for the dehydrogenation of dehydrogenatable hydrocarbons utilizing the improved catalytic composite. Accordingly, in a broad embodiment, the present invention is a catalytic composite comprising a first component selected from Group VIII noble metal components or mixtures thereof, a second component in an amount from 0.9 to 1.1 weight percent, based on the total composite weight selected from the group consisting of alkali or alkaline earth metal components or mixtures thereof and a third component selected from the group consisting of tin, germanium, lead, indium, gallium, thallium and mixtures thereof, all on an alumina support comprising essentially theta-alumina and having a surface area from about 50 to about 120 $m^2/g$ and an apparent bulk density of at least 0.5 $g/cm^3$ wherein the mole ratio of the first component to the third component is in the range from about 1.5 to about 1.7.

Another embodiment of the present invention is a catalytic composite comprising platinum, potassium in an amount from 0.9 to 1.1 weight percent, based on the total composite weight and a third component selected from the group consisting of tin, germanium, lead, indium, gallium, thallium and mixtures thereof, all on an alumina support, the catalytic composite characterized in that the alumina comprises essentially theta-alumina, has a surface area from about 50 to about 120 $m^2/g$, an apparent bulk density of greater than about 0.6 $g/cm^3$ and a platinum to third component mole ratio from about 1.5 to about 1.7.

In yet another embodiment, the invention is a hydrocarbon dehydrogenation process comprising the steps of contacting a hydrocarbon at dehydrogenation conditions with a catalytic composite comprising a first component selected from Group VIII noble metal components or mixtures thereof, a second component in an amount from 0.9 to 1.1 weight percent, based on the total composite weight selected from the group consisting of alkali or alkaline earth metal components or mixtures thereof and a third component selected from the group consisting of tin, germanium, lead, indium, gallium, thallium and mixtures thereof, all on an alumina support comprising essentially theta-alumina and having a surface area from about 50 to about 120 $m^2/g$ and an apparent bulk density of at least 0.5 $g/cm^3$ wherein the mole ratio of the first component to the third component is in the range from about 1.5 to about 1.7.

DESCRIPTION OF THE FIGURE

The FIGURE is a graph plotting propane conversion versus total is hours on stream comparing two prior art catalysts with the catalyst of the present invention.

DETAILED DESCRIPTION OF THE INVENTION

To summarize, the present invention is an improved catalytic composite as well as a process for the use of the catalytic composite.

One essential feature of the present invention lies in the characteristics of the support for the instant catalyst. Specifically, it is important that the alumina catalyst support have a surface area of 120 $m^2/g$ or less and a corresponding Apparent Bulk Density (ABD) of 0.5 $g/cm^3$ or greater. The support comprises a number of catalytic components including a Group VIII noble metal component, an alkali or alkaline earth component, and a component selected from the group consisting of tin, germanium, lead, indium, gallium, thallium, or mixtures thereof. Another essential feature of the present invention is that the mole ratio of the Group VIII noble metal to the component selected from the group consisting of tin, germanium, lead, indium, gallium, thallium, or mixtures thereof is in the range from about 1.5 to about 1.7. Such a catalyst exhibits improved catalyst conversion in a hydrocarbon dehydrogenation process in comparison to similar dehydrogenation catalysts of the prior art. In addition, it has been discovered that when the preferred mole ratio is used, the catalyst demonstrates a higher initial maximum hydrocarbon dehydrogenation activity.

As indicated above, one essential feature of the catalytic composite of the invention is a first component selected from Group VIII noble metals or mixtures thereof. The Group VIII noble metal may be selected from the group consisting of platinum, palladium, iridium, rhodium, osmium, ruthenium, or mixtures thereof. Platinum, however, is the preferred Group VIII noble metal component.

Preferably the Group VIII noble metal component is well dispersed throughout the catalyst. It generally will comprise about 0.01 to 5 wt. %, calculated on an elemental basis, of the final catalytic composite. Preferably, the catalyst comprises about 0.1 to 2.0 wt. % Group VIII noble metal component, especially about 0.1 to about 2.0 wt. % platinum.

The Group VIII noble metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the alumina support with a solution or suspension of a decomposable compound of a Group VIII noble metal. For example, platinum may be added to the support by commingling the latter with an aqueous solution of chloroplatinic acid. Another acid, for example, nitric acid or other optional components, may be added to the impregnating solution to further assist in evenly dispersing or fixing the Group VIII noble metal component in the final catalyst composite.

Another essential feature of the catalyst of this invention is a second catalytic component comprised of an alkali or alkaline earth component. The alkali or alkaline earth component of the present invention may be selected from the group consisting of cesium, rubidium, potassium, sodium, and lithium or from the group consisting of barium, strontium, calcium, and magnesium or mixtures of metals from either or both of these groups. Potassium, however, is the preferred second catalytic component. It is believed that the alkali and alkaline earth component exists in the final catalytic composite in an oxidation state above that of the elemental metal. The alkali and alkaline earth component may be present as a compound such as the oxide, for example, or combined with the carrier materiel or with the other catalytic components.

Preferably the alkali and alkaline earth component is well dispersed throughout the catalytic composite. The alkali or alkaline earth component will preferably comprise 0.9 to 1.1 wt. %, calculated on an elemental basis of the final catalytic composite.

The alkali or alkaline earth component may be incorporated in the catalytic composite in any suitable manner such as, for example, by coprecipitation or cogelation, by ion exchange or impregnation, or by like procedures either before, while, or after other catalytic components are incorporated. A preferred method of incorporating the alkali component is to impregnate the carrier material with a solution of potassium hydroxide.

A third essential component of the catalyst of the present invention is a modifier metal component selected from the group consisting of tin, germanium, lead, indium, gallium, thallium, and mixtures thereof. The effective amount of the third modifier metal component is preferably uniformly impregnated. Generally, the catalyst will comprise from about 0.01 to about 10 wt. % of the third modifier metal component calculated on an elemental basis on the weight of the final composite. Preferably, the catalyst will comprise from about 0.1 to about 5 wt. % of the third modifier metal component.

The third modifier metal component of the present invention preferably is tin. Some or all of the tin component may be present in the catalyst in an oxidation state above that of the elemental metal. This component may exist within the composite as a compound such as the oxide, sulfide, halide, oxychloride, aluminate, etc., or in combination with the carrier material or other ingredients of the composite. Preferably, the tin component is used in an amount sufficient to result in the final catalytic composite containing, on an elemental basis, about 0.01 to about 10 wt. % tin, with best results typically obtained with about 0.1 to about 5 wt. % tin.

Suitable tin salts or water-soluble compounds of tin which may be used include stannous bromide, stannous chloride, stannic chloride, stannic chloride pentahydrate, stannic chloride tetrahydrate, stannic chloride trihydrate, stannic chloride diamine, stannic trichloride bromide, stannic chromate, stannous fluoride, stannic fluoride, stannic iodide, stannic sulfate, stannic tartrate, and the like compounds. The utilization of a tin chloride compound, such as stannous or stannic chloride is particularly preferred.

The third component of the catalyst may be composited with the support in any sequence. Thus, the first or second component may be impregnated on the support followed by sequential surface or uniform impregnation of the third component. Alternatively, the third component may be surface or uniformly impregnated on the support followed by impregnation of the other catalytic component.

The catalytic composite of this invention may also contain a halogen component. The halogen component may be fluorine, chlorine, bromine, or iodine, or mixtures thereof. Chlorine is the preferred halogen components. The halogen component is generally present in a combined state with the porous carrier material and alkali component. Preferably, the halogen component is well dispersed throughout the catalytic composite. The halogen component may comprise from more than 0.01 wt. % to about 15 wt. %, calculated on an elemental basis, of the final catalytic composite.

The halogen component may be incorporated in the catalytic composite in any suitable manner, either during the preparation of the carrier material or before, while, or after other catalytic components are incorporated. For example, the alumina sol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound or solution containing the halogen before or after other catalyst components are incorporated with the carrier material. Suitable compounds containing the halogen include acids containing the halogen, for example, hydrochloric acid. Or, the halogen component or a portion thereof may be incorporated by contacting the catalyst with a compound or solution containing the halogen in a subsequent catalyst regeneration step. In the regeneration step, carbon deposited on the catalyst as coke during use of the catalyst in a hydrocarbon conversion process is burned off and the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process. The halogen may also be added as chlorine gas ($Cl_2$).

The carrier material of the present invention is alumina having a surface area less than 120 $m^2/g$. In addition, the catalyst carrier alumina should have an ABD of 0.5 $g/cm^3$ or more. The alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16-inch in diameter, though particles as small as about 1/32-inch and smaller may also be utilized.

To make alumina spheres, aluminum metal is converted into an alumina sol by reacting it with a suitable peptizing agent and water, and then dropping a mixture of the sol into an oil bath to form spherical particles of the alumina gel. It is also an aspect of this invention that the third modifier metal component may be added to the alumina sol before it is reacted with a peptizing agent and dropped into the hot oil bath. Other shapes of the alumina carrier material may also be prepared by conventional methods. After the alumina particles optionally containing the co-formed third component are shaped, they are dried and calcined.

It is the drying and calcination of the alumina base component that is most important in imparting the catalyst base with the desired characteristics of this invention. It is important that the catalyst alumina base of this invention have a surface area of 120 $m^2/g$ or less and a corresponding ABD of 0.50 $g/cm^3$ or more. These characteristics are imparted in the alumina by a final calcination of the alumina at a temperature ranging from 950° to 1200° C. It is preferable that the final calcination step be at conditions sufficient to convert the alumina into theta-alumina which conforms to the desired characteristics of the alumina base of the instant catalyst. Such conditions would include a calcination temperature closely controlled between 950° and 1100° C. and preferably from 975° to 1050° C.

It is to be understood that the surface area of the catalyst as set forth in the description of the invention and the appended claims are derived by the well-known mercury intrusion technique. This method may be used for determining the pore size distribution and pore surface area of porous substances by mercury intrusion using a Micromeritics Auto Pore 9200 Analyzer. In this method, high pressure mercury is forced into the pores of the catalyst particles at incrementally increasing pressures to a maximum of 413,700 kPa (60,000 psia). Pore volume readings are taken at predetermined pressures. A maximum of 85 pressure points can be chosen. Accordingly by this method, a thorough distribution of pore volumes may be determined.

The effect of calcination of an alumina base especially at the elevated temperatures disclosed in this invention is to densify the alumina base. The densification, i.e. increase in ABD, is caused by a decrease in the overall catalyst pore volume. In addition, the high calcination temperatures cause the existing pores to expand. To accomplish this apparently contradictory mechanism, the catalyst necessarily contracts in size while the existing pores expand. By expanding, the mouths of the existing pores increase so that they become less likely to be plugged or restricted by coke build-up.

It is preferred that the alumina component is essentially theta-alumina. By "essentially theta-alumina", it is meant that at least 75% of the alumina crystallites are theta-alumina crystallites. The remaining crystallites of alumina will likely be in the form of alpha-alumina or gamma-alumina. However, other forms of alumina crystallites known in the art may also be present. It is most preferred if the essentially theta-alumina component comprises at least 90% crystallites of theta-alumina.

As explained, the theta-alumina form of crystalline alumina is produced from the amorphous alumina precursor by closely controlling the maximum calcination temperature experienced by the catalyst support. Calcination temperatures ranging from 800° to 950° C. are known to produce alumina comprising essentially crystallites of gamma-alumina. Calcination temperatures of 1100° C. and above are known to promote the formation of alpha-alumina crystallites while temperatures of from 950° to 1100° C. and especially from 975° to 1050° C. promote the formation of theta-alumina crystallites.

After the catalyst components have been combined with the desired alumina support, the resulting catalyst composite will generally be dried at a temperature of from about 100° to about 320° C. for a period of typically about 1 to 24 hours or more and thereafter calcined at a temperature of about 320° to about 600° C. for a period of about 0.5 to about 10 or more hours. Typically, chlorine-containing compounds are added to air to prevent sintering of catalyst metal components. This final calcination typically does not affect the alumina crystallites or ABD. However, the high temperature calcination of the support may be accomplished at this point if desired. Finally, the calcined catalyst composite is typically subjected to a reduction step before use in the hydrocarbon conversion process. This reduction step is effected at a temperature of about 230° to about 650° C. for a period of about 0.5 to about 10 or more hours in a reducing environment, preferably dry hydrogen, the temperature and time being selected to be sufficient to reduce substantially all of the platinum group component to the elemental metallic state.

As indicated above, the catalyst of the present invention has particular utility as a hydrocarbon conversion catalyst. The hydrocarbon which is to be converted is contacted with the catalyst at hydrocarbon conversion conditions. These conditions include a temperature of from about 200° to 1000° C., a pressure of from 0.25 atmospheres absolute (ATMA) to about 25 atmospheres gauge, and liquid hourly space velocities of from about 0.1 to about 200 hr$^{-1}$.

According to one embodiment, the hydrocarbon conversion process of the invention is dehydrogenation. In the preferred process, dehydrogenatable hydrocarbons are contacted with the catalytic composite of the instant invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred in one preferred embodiment. In this fixed bed system, the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to ensure that the desired reaction temperature can be maintained at the entrance to each reaction zone. The hydrocarbon may be contacted with the catalyst bed in either upward, downward, or radial flow fashion. Radial flow of the hydrocarbon through the catalyst bed is preferred for commercial scale reactors. The hydrocarbon may be in the liquid phase, a mixed vapor-liquid phase, or the vapor phase when it contacts the catalyst. Preferably, it is in the vapor phase.

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of $C_2$–$C_6$ paraffins, primarily propane and butanes, to monoolefins.

Dehydrogenation conditions include a temperature of from about 400° to about 900° C., a pressure of from about 0.01 to 10 atmospheres absolute, and a liquid hourly space velocity (LHSV) of from about 0.1 to 100 hr$^{-1}$. Generally for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while, or after being passed to the dehydrogenation zone. The diluent material may be hydrogen, steam, methane, ethane, carbon dioxide, nitrogen, argon, and the like or a mixture thereof. Hydrogen and steam are the preferred diluents. Ordinarily, when hydrogen or steam is utilized as the diluent, it is utilized in amounts sufficient to ensure a diluent-to-hydrocarbon mole ratio of about 0.1:1 to about 40:1, with best results being obtained when the mole ratio range is about 0.4:1 to about 10:1. The diluent stream passed to the dehydrogenation zone will typically be recycled diluent separated from the effluent from the dehydrogenation zone in a separation zone.

A combination of diluents, such as steam with hydrogen, may be employed. When hydrogen is the primary diluent water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins have from 6 to 30 or more carbon atoms.

To be commercially successful, a dehydrogenation catalyst should exhibit three characteristics, namely, high activity, high selectivity, and good stability. Activity is a measure of the catalyst's ability to convert reactants into products at a specific set of reaction conditions, that is, at a specified temperature, pressure, contact time, and concentration of diluent such as hydrogen, if any. For dehydrogenation catalyst activity, the conversion or disappearance of paraffins in percent relative to the amount of paraffins in the feedstock is measured. Selectivity is a measure of the catalyst's ability to convert reactants into the desired product or products relative to the amount of reactants converted. For catalyst selectivity, the amount of olefins in the product, in mole percent, relative to the total moles of the paraffins converted is measured. Stability is a measure of the rate of change with time on stream of the activity and selectivity parameters—the smaller rates implying the more stable catalysts.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. In an improvement, processes have been developed which utilize a two-catalyst system with distinct beds or reactors of dehydrogenation or selective oxidation catalysts. The purpose of the selective oxidation catalysts is to selectively oxidize the hydrogen produced as a result of the dehydrogenation reaction with oxygen that had been added to the oxidation zone to generate heat internally in the process. The heat generated typically is sufficient to cause the reaction mixture to reach desired dehydrogenation temperatures for the next dehydrogenation step. The instant process may be accomplished in this previously mentioned system. If such a process is employed, the instant catalyst would comprise at least the dehydrogenation catalyst with another specific catalyst being used to accomplish the oxidation reaction. Before explaining the preferred reactor configurations, more details of the oxidation aspect of the invention are disclosed.

The selective oxidation step, if utilized, uses the hydrogen which has been produced in the dehydrogenation step of the process to supply heat to the next dehydrogenation reaction section. To accomplish this, an oxygen-containing gas is first introduced into the reactor, preferably at a point adjacent to the selective oxidative catalyst section. The oxygen in the oxygen-containing gas is necessary to oxidize the hydrogen contained in the reaction stream. Examples of oxygen-containing gases which may be utilized to effect the selective oxidation of the hydrogen which is present will include air, oxygen, or air or oxygen diluted with other gases such as steam, carbon dioxide and inert gases such as nitrogen, argon, helium, etc. The amount of oxygen which is introduced to contact the process stream may range from about 0.01:1 to about 2:1 moles of oxygen per mole of hydrogen contained in the process stream at the point where oxygen is added to the process stream. In the selective oxidation reaction, the process stream which comprises unreacted dehydrogenatable hydrocarbon, dehydrogenated hydrocarbon, and hydrogen is reacted with oxygen in the presence of the selective steam oxidation/dehydrogenation catalyst whereby hydrogen is selectively oxidized to produce water and heat energy with very little of the oxygen reacting with the hydrocarbons.

The selective steam oxidation/dehydrogenation catalyst may be one that is useful for the selective oxidation of hydrogen in the presence of hydrocarbons. An example of such a catalyst is disclosed in U.S. Pat. No. 4,418,237. Alternatively, the catalyst used for the selective oxidation step may be identical to the catalyst utilized for the dehydrogenation step. Such catalysts or processes for their use are disclosed in U.S. Pat. Nos. 4,613,715 and 3,670,044. The instant catalyst exhibits both dehydrogenation and selective oxidation functions. Therefore, it is possible that the catalyst of this invention could be used in a single catalyst containing a process for the dehydrogenation and selective oxidation of hydrocarbons.

The oxygen-containing reactant may be added to the instant process in various ways such as by admixing oxygen with a relatively cool hydrocarbon feed stream or with the steam diluent, or it may be added directly to the reactor independently of the feed hydrocarbons or the steam diluent. In addition, the oxygen-containing reactant can be added at one or more points in the reactor in such a fashion as to minimize local concentrations of oxygen relative to hydrogen in order to distribute the beneficial temperature rise produced by the selective hydrogen oxidation over the entire length of the reaction zone. In fact, using a plurality of injection points for introducing the oxygen-containing gas into the steam oxidation/dehydrogenation reaction zone is a preferred mode of operation. This procedure minimizes the opportunity for local build-up of the concentration of oxygen relative to the amount of hydrogen, thereby minimizing the opportunity for undesired reaction of the oxygen-containing gas with either feed or product hydrocarbons.

The following example is introduced to further describe the catalyst and process of the invention. This example is intended as an illustrative embodiment and should not be considered to restrict the otherwise broad interpretation of the invention as set forth in the claims appended hereto.

EXAMPLE

In accordance with the present invention, the dehydrogenation of a hydrocarbon deactivates the dehydrogenation catalyst in about 100 hours of operation before it is necessary to regenerate the catalyst. Therefore, the activity of a dehydrogenation catalyst is graded by its initial maximum activity and its performance over a period of time from 5 to about 20 hours on stream.

In order to demonstrate the advantages to be achieved by the present invention, a catalyst of this invention and two state of the art prior art catalysts were prepared.

The first prior art catalyst contained 0.2 weight percent tin and 0.7 weight percent potassium and the second prior catalyst contained 0.2 weight percent tin and 1 weight percent potassium. The catalyst of the present invention contained 0.17 weight percent tin and 1 weight percent potassium. These catalysts are identified as Catalyst A, Catalyst B and Catalyst C, respectively. First for all three catalysts, a spherical alumina support was prepared by the well-known oil-drop method. A tin component was incorporated in the support by commingling a tin component precursor with the alumina hydrosol and thereafter gelling the hydrosol. The tin component in this case was uniformly distributed throughout the catalyst particles. The catalyst particles were then dried at 600° C. for about 2 hours and calcined at about 1050° C. The calcined tin-containing particles were then contacted with a chloroplatinic acid solution and a potassium hydroxide solution to uniformly impregnate the alumina base with platinum and potassium. After impregnation, the catalyst was oven-treated in air at about 500° C. for 4 hours in the presence of 3% steam and chlorine-containing gases, followed by reduction in hydrogen at about 550° C. for about 2 hours. Catalyst A (prior art catalyst) was prepared in accordance with the above-described method to produce a finished catalyst containing 0.45 weight percent platinum, 0.7 weight percent potassium and 0.2 weight percent tin and having a platinum to tin mole ratio of 1.37. Catalyst B (prior art catalyst) was also prepared in accordance with the above-described method to produce a finished catalyst containing 0.45 weight percent platinum, 1.0 weight percent potassium and 0.2 weight percent tin and having a platinum to tin mole ratio of 1.37. Catalyst C (invention) was similarly prepared to produce a finished catalyst containing 0.45 weight percent platinum, 1.0 weight percent potassium and 0.17 weight percent tin and having a platinum to tin mole ratio of 1.6. The properties of the catalysts are presented in Table 1 for comparison.

Each catalyst in turn was tested in a pilot plant to dehydrogenate propane to produce propylene. The operating conditions of each pilot plant test included a hydrogen to propane mole ratio of 0.4, a liquid hourly space velocity (LHSV) of 30 hr$^{-1}$, a pressure of 135 kPa (5 psig) and a feed temperature of 655° C. (1210° F.). The results of the tests are presented in the FIGURE demonstrating the propane conversion plotted against the total hours on stream.

From the FIGURE, it can be seen that the catalyst of the present invention (Catalyst C) demonstrates a higher initial maximum activity and achieves a higher propane conversion from 5 to 20 hours on stream than the prior art catalysts at the same operating conditions. The lowering of the tin content from 0.20 to 0.17 weight percent with a potassium content of 1 weight percent while maintaining the same platinum level of 0.45 weight percent increases the platinum to tin mole ratio from 1.37 to 1.6 and thereby surprisingly achieves a catalyst having increased activity for the dehydrogenation of propane.

TABLE 1

|  | Catalyst A Prior Art | Catalyst B Prior Art | Catalyst C Invention |
|---|---|---|---|
| Calcination Temp., ° C. | 1050 | 1050 | 1050 |
| Surface area m$^2$/g | 80 | 80 | 80 |
| ABD, g/cm$^3$ | 0.60 | 0.60 | 0.60 |
| Platinum, weight percent | 0.45 | 0.45 | 0.45 |
| Tin, weight percent | 0.20 | 0.20 | 0.17 |
| Potassium, weight percent | 0.7 | 1.0 | 1.0 |
| Platinum/Tin, mole ratio | 1.37 | 1.37 | 1.6 |

The foregoing description, FIGURE and example clearly illustrate the advantages encompassed by the process of the present invention and the benefits to be afforded with the use thereof.

What is claimed:

1. A catalytic composite comprising a first component selected from the group consisting of Group VIII noble metal components and mixtures thereof, a second component in an amount of from 0.9 to 1.1 weight percent, based on the total composite weight, selected from the group consisting of alkali metal components, alkaline earth metal components, and mixtures thereof, and a third component selected from the group consisting of tin, germanium, lead, indium, gallium, thallium, and mixtures thereof, all supported on an alumina support comprising essentially theta-alumina, said support having a surface area of from about 50 to about 120 m$^2$/g and an apparent bulk density of at least 0.5 g/cm$^3$, and wherein the mole ratio of the first component to the third component is in the range of from about 1.5 to about 1.7.

2. The catalytic composite of claim 1 wherein the first component is platinum.

3. The catalytic composite of claim 1 wherein the second component is potassium.

4. The catalytic composite of claim 1 wherein the third component is tin.

5. A catalytic composite comprising platinum, potassium in an amount of from 0.9 to 1.1 weight percent, based on the total composite weight, and another component selected from the group consisting of tin, germanium, lead, indium, gallium, thallium, and mixtures thereof, all supported on an alumina support, said alumina comprises essentially of theta-alumina, which has a surface area of from about 50 to about 120 m$^2$/g, an apparent bulk density of greater than about 0.6 g/cm$^3$, and a mole ratio of platinum to said another component of from about 1.5 to about 1.7.

6. The catalytic composite of claim 5 wherein the another component is tin.

7. The catalytic composite of claim 5 wherein the catalyst comprises from about 0.01 to about 5 weight percent platinum, from 0.9 to 1.1 weight percent potassium and from about 0.01 to about 5 weight percent tin.

* * * * *